US00PP17804P2

(12) United States Plant Patent
Lang

(10) Patent No.: US PP17,804 P2
(45) Date of Patent: Jun. 12, 2007

(54) ***OSTEOSPERMUM* PLANT NAMED 'LANAFLO'**

(50) Latin Name: *Osteospermum ecklonis*
Varietal Denomination: Lanaflo

(76) Inventor: Robin Lang, 14 Kingsway, Tiptree, Essex, CO5 0LS (GB)

( * ) Notice: Subject to any disclaimer, the term of this patent is extended or adjusted under 35 U.S.C. 154(b) by 0 days.

(21) Appl. No.: 11/311,672

(22) Filed: Dec. 19, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Osteospermum* plant named 'Lanaflo', characterized by its compact, upright, somewhat outwardly spreading and mounded plant habit; freely branching habit; early and freely flowering habit; inflorescences with bright yellow-colored ray florets tinged with orange at the apices; and tolerance to high temperatures.

1 Drawing Sheet

Botanical designation: *Osteospermum ecklonis.*
Botanical denomination: 'Lanaflo'.

BACKGROUND OF THE INVENTION

The present Invention relates to a new and distinct cultivar of *Osteospermum* plant, botanically known as *Osteospermum ecklonis,* and hereinafter referred to by the name 'Lanaflo'.

The new *Osteospermum* is a product of a planned breeding program conducted by the Inventor in Tiptree, Essex, United Kingdom. The objective of the breeding program was to create new *Osteospermum* cultivars with uniform and freely branching plant habit, unique and attractive floret coloration, and tolerance to high temperatures.

The new *Osteospermum* originated from a cross-pollination during the spring of 2002 of a proprietary *Osteospermum ecklonis* selection identified as code number 09-49-01, not patented, as the female, or seed, parent with an unidentified proprietary seedling selection of *Osteospermum ecklonis,* not patented, as the male, or pollen, parent. The new *Osteospermum* was discovered and selected by the Inventor as a single flowering plant within the progeny of the stated cross-pollination grown in a controlled environment in Tiptree, Essex, United Kingdom in 2003. The new *Osteospermum* was selected on the basis of its compact and freely branching plant habit, attractive ray floret coloration and tolerance to high temperatures.

Asexual reproduction of the new *Osteospermum* by terminal vegetative cuttings has shown that the unique features of this new *Osteospermum* are stable and reproduced true to type in successive generations.

SUMMARY OF THE INVENTION

The cultivar Lanaflo has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Lanaflo'. These characteristics in combination distinguish 'Lanaflo' as a new and distinct *Osteospermum:*

1. Compact, upright, somewhat outwardly spreading and mounded plant habit.
2. Freely branching habit.
3. Early and freely flowering habit.
4. Inflorescences with bright yellow-colored ray florets tinged with orange at the apices.
5. Tolerant to high temperatures.

Plants of the new *Osteospermum* differ primarily from plants of the parent selections in ray floret coloration.

Plants of the new *Osteospermum* can be compared to plants of the cultivar Cape Daisy Zulu, disclosed in U.S. Plant Pat. No. 10,389. However, in side-by-side comparisons conducted in Tiptree, Essex, United Kingdom, plants of the new *Osteospermum* differed from plants of the cultivar Cape Daisy Zulu in the following characteristics:

1. Plants of the new *Osteospermum* had smaller leaves than plants of the cultivar Cape Daisy Zulu.
2. Plants of the new *Osteospermum* were more freely branching than plants of the cultivar Cape Daisy Zulu.
3. Plants of the new *Osteospermum* were more freely flowering than plants of the cultivar Cape Daisy Zulu.
4. Plants of the new *Osteospermum* and the cultivar Cape Daisy Zulu differed in ray floret coloration as plants of the cultivar Cape Daisy Zulu had yellow-colored ray florets.
5. Plants of the new *Osteospermum* and the cultivar Cape Daisy Zulu differed in disc coloration as plants of the cultivar Cape Daisy Zulu had yellowish brown-colored discs.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum*.

The photograph at the top of the sheet comprises a top perspective view of a typical flowering plant of 'Lanaflo' grown in a container.

The photograph at the bottom of the sheet is a close-up view of a typical inflorescence of 'Lanaflo'.

DETAILED BOTANICAL DESCRIPTION

The new *Osteospermum* has not been observed under all possible environmental conditions. The phenotype may vary somewhat with variations in environment such as temperature and light intensity, without, however, any variance in genotype.

The aforementioned photographs, following observations and measurements describe plants grown in Tiptree, Essex, United Kingdom in a glass-covered greenhouse and under typical production practices. Plants were about five months old when the photographs and description were taken. Plants were grown in 15-cm containers and were pitched one time. During the production of the plants, day temperatures averaged 19° C. and night temperatures averaged 14° C. In the following description, color references are made to The Royal Horticultural Society Colour Chart, 2001 Edition, except where general terms of ordinary dictionary significance are used.

Botanical classification: *Osteospermum ecklonis* cultivar Lanaflo.

Parentage:

*Female, or seed, parent.*—Proprietary selection of *Osteospermum ecklonis* identified as code number 09-49-01, not patented.

*Male, or pollen, parent.*—Unidentified proprietary seedling selection of *Osteospermum ecklonis,* not patented.

Propagation:

*Type.*—Terminal vegetative cuttings.

*Time to initiate rooting.*—About two weeks at 20° C.

*Time to produce a rooted young plant.*—About one month at 20° C.

*Root description.*—Fine, fibrous; white in color.

*Rooting habit.*—Freely branching.

Plant description:

*Plant form and growth habit.*—Perennial herbaceous container and garden plant. Compact, upright, somewhat outwardly spreading and mounded plant habit. Freely branching habit, about five primary lateral branches and numerous secondary lateral branches. Moderately vigorous growth habit.

*Plant height.*—About 17 cm.

*Plant width or area of spread.*—About 16.5 cm.

*Lateral branches.*—Length: About 4.8 cm. Diameter: About 4 mm. Internode length: About 3 mm. Aspect: Upright and somewhat outwardly spreading. Strength: Strong. Texture: Sparsely pubescent. Color: 143B.

*Foliage description.*—Arrangement: Alternate, simple; sessile. Length: About 4.9 cm. Width: About 1.4 cm. Shape: Oblanceolate to obovate with protruding points. Apex: Acute to obtuse. Base: Cuneate. Margin: Entire with six protruding points. Venation pattern: Pinnate. Texture, upper and lower surfaces: Smooth, glabrous; towards the margins, sparsely pubescent. Color: Developing foliage, upper surface: Between 137A and 143A. Developing foliage, lower surface: 137C. Fully expanded foliage, upper surface: 137A; venation, 143A. Fully expanded foliage, lower surface: 137B; venation, 143A to 143B.

Inflorescence description:

*Appearance.*—Solitary terminal and axillary inflorescences held above and beyond the foliage on strong peduncles. Composite inflorescence form, radially symmetrical, with narrowly oblanceolate-shaped ray florets and disc florets massed at the center; ray and disc florets develop acropetally on a capitulum. Inflorescences persistent. Inflorescences face mostly upright.

*Flowering response.*—Early flowering; plants flower continuous and freely from the late spring until the early autumn in the United Kingdom.

*Postproduction longevity.*—Inflorescences maintain good color and substance for about two weeks on the plant.

*Quantity of inflorescences.*—Freely flowering; at one time, about six inflorescences per lateral stem.

*Fragrance.*—None detected.

*Inflorescence bud.*—Length: About 1.2 cm. Diameter: About 1 cm. Shape: Broadly elliptic. Color: 144A.

*Inflorescence size.*—Diameter: About 5.8 cm. Depth (height): About 2.6 cm. Disc diameter: About 1.1 cm. Receptacle height: About 1.5 cm. Receptacle diameter: About 1.9 cm.

*Ray florets.*—Length: About 2.8 cm. Width: About 7 mm. Shape: Narrowly oblanceolate. Apex: Praemorse. Base: Attenuate. Margin: Entire. Texture, upper and lower surfaces: Smooth, glabrous. Orientation: Initially upright then about 80° from vertical. Number of ray florets per inflorescence: About 25 in one to two whorls. Color: When opening, upper surface: 17A; towards the base, 12A. When opening, lower surface: 12A. Fully opened, upper surface: 12A; towards the base, 12B; apices tinged with close to N163A. Fully opened, lower surface: 13B; central band, 177B to 177C.

*Disc florets.*—Shape: Tubular, elongated. Apex: Five-pointed. Length: About 4 mm. Width: At apex: About 1.3 mm. At base: About 0.8 mm. Number of disc florets per inflorescence: About 100. Color: Immature: 145D. Mature: Apex: N186B. Mid-section: 63B. Base: 149D.

*Phyllaries.*—Length: About 1.1 cm. Diameter: About 1.4 mm. Shape: Linear. Apex: Acute. Base: Cuneate. Margin: Entire. Texture, upper and lower surfaces: Sparsely pubescent. Number per inflorescence: About 19 in a single whorl. Color, upper and lower surfaces: 143A.

*Peduncles.*—Length, terminal peduncle: About 6.9 cm. Length, fourth peduncle: About 4.3 cm. Diameter: About 2 mm. Angle: Terminal peduncles, mostly upright; axillary peduncles about 35° from stem axis. Strength: Strong. Texture: Sparsely pubescent. Color: 143A.

*Reproductive organs.*—Androecium: Present on disc florets only. Stamen number: Five per floret; fused around style. Anther shape: Lanceolate. Anther length: About 3 mm. Anther color: N92C. Pollen amount: Moderate. Pollen color: 25A. Gynoecium: Present on both ray and disc florets. Pistil number: One per floret. Pistil length: About 8 mm. Stigma shape: Two-parted. Stigma color: 187A. Style length: About 7 mm. Style color: 145D. Ovary color: 145D.

*Seed/fruit.*—Seed and/or fruit production has not been observed.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from about 0° C. to 35° C.

It is claimed:

1. A new and distinct cultivar of *Osteospermum* plant named 'Lanaflo', as illustrated and described.

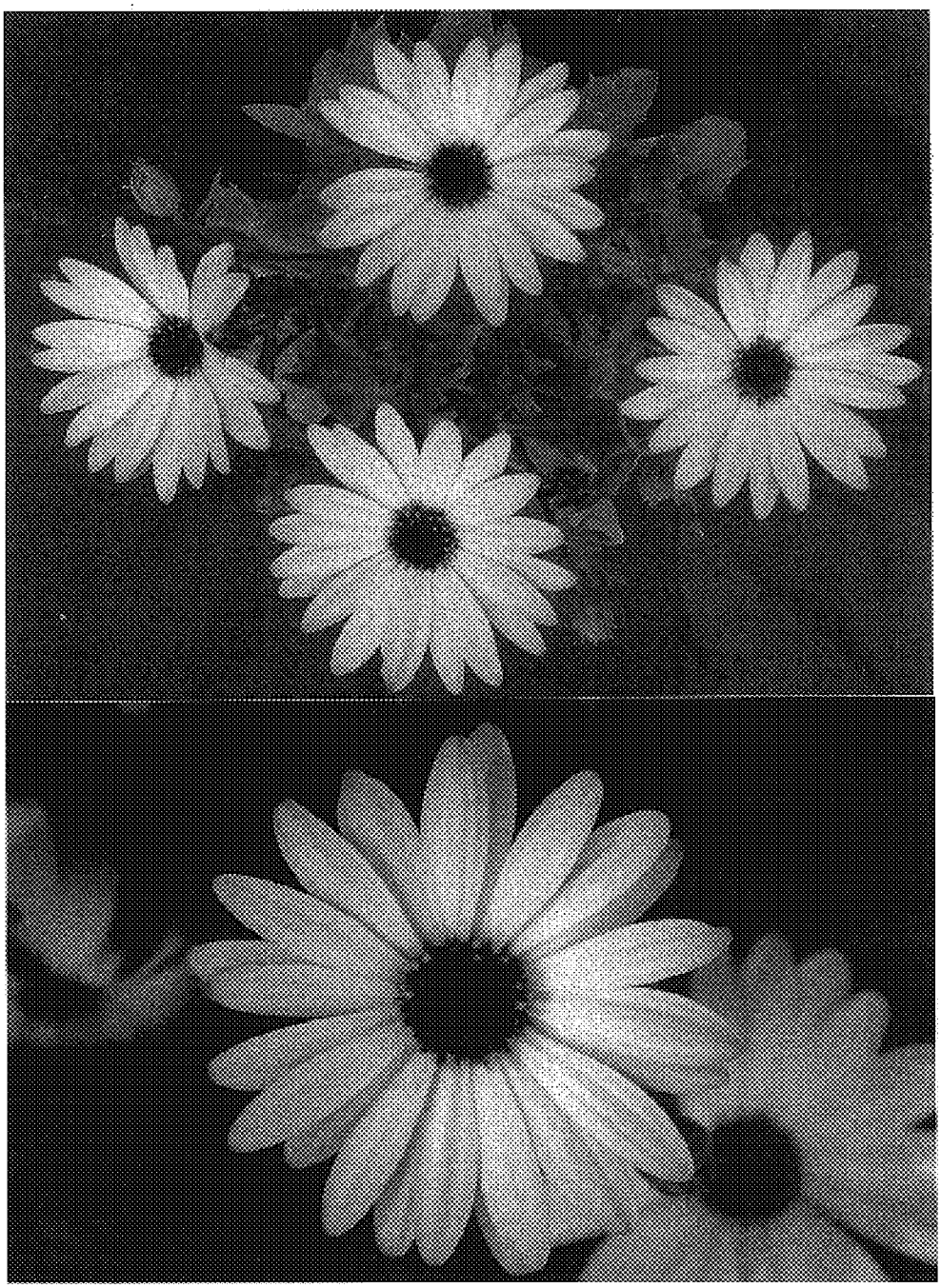

* * * * *